United States Patent

Bloom et al.

[11] 4,089,866
[45] May 16, 1978

[54] CERTAIN BENZOTHIAZOLIUM COMPOUNDS

[75] Inventors: Stanley M. Bloom, Waban; Alan L. Borror, Lexington; Richard B. Greenwald, Cambridge, all of Mass.

[73] Assignee: Polaroid Corporation, Cambridge, Mass.

[21] Appl. No.: 741,240

[22] Filed: Nov. 12, 1976

Related U.S. Application Data

[60] Continuation-in-part of Ser. No. 590,144, Jun. 25, 1975, Pat. No. 4,006,151, which is a continuation-in-part of Ser. No. 399,456, Sep. 21, 1973, abandoned, which is a division of Ser. No. 261,270, Jun. 9, 1972, Pat. No. 3,794,485.

[51] Int. Cl.² .............................................. C07D 277/64
[52] U.S. Cl. .................................. 260/304 C; 8/115.6; 542/422
[58] Field of Search .................................... 260/304 C Primary Examiner—Richard J. Gallagher
Attorney, Agent, or Firm—Philip G. Kiely

[57] ABSTRACT

Novel substantially colorless dye precursors represented by the formula

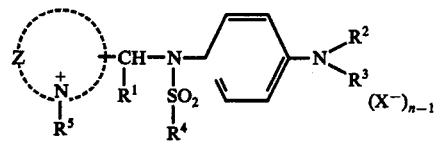

wherein $R^1$ is hydrogen or alkyl; $R^2$, $R^3$ and $R^5$ is alkyl; $R^4$ is alkyl or phenyl; Z, taken with N, represents the atoms necessary to make a benzthiazole radical; X is an acid anion; and $n$ is 1 when $R^5$ carries a negative charge and 2 when $R^5$ is electrically neutral.

8 Claims, No Drawings

CERTAIN BENZOTHIAZOLIUM COMPOUNDS

CROSS-REFERENCE TO OTHER APPLICATIONS

This application in a continuation-in-part of U.S. patent application Ser. No. 590,144 filed June 25, 1975 now U.S. Pat. No. 4,006,151, issued Feb. 1, 1977; which in turn is a continuation-in-part of U.S. Pat. application Ser. No. 399,456 filed Sept. 21, 1973 now abandoned; which is a division of U.S. patent application Ser. No. 261,270 filed June 9, 1972; now U.S. Pat. No. 3,794,485 issued Feb. 26, 1974.

BACKGROUND OF THE INVENTION

U.S. Pat. No. 3,794,465 discloses photographic film units which incorporate intermediate the photosensitive silver halide emulsion layer and a transparent support, a substantially colorless precursor of a dye. This precursor is converted into a dye, a colored species which will absorb light which otherwise might fog the photoexposed silver halide emulsion. Since the precursor is initially colorless, the location of the precursor in the film unit does not interfere with the exposure of the silver halide emulsion. The precursor is converted to its colored form by contact with alkali.

In a preferred embodiment, the dye produced from the above-described precursor is a silver halide desensitizing agent. Thus, instead of a light filtering mechanism, a silver halide desensitizing mechanism may be employed to protect the silver halide emulsion layer from post-exposure fogging. While the same materials can be employed to perform the two described functions, it should be understood that the quantity employed is generally much less for the silver halide desensitizing agent than for the filter dye.

The present invention is directed to novel compositions for use as the above-described dye precursors.

SUMMARY

The novel compounds of the present invention comprise a substantially colorless precursor of a β-azadisubstituted amino styryl dye represented by the formula:

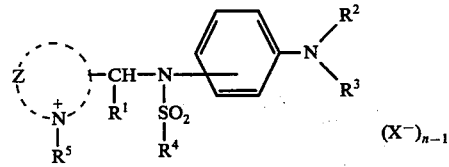

wherein $R^1$ is hydrogen or alkyl; preferably 1 to 4 carbon alkyl; $R^2$ $R^3$ and $R^5$ are alkyl, preferably 1 to 4 carbon alkyl, more preferably, methyl or ethyl; $R^4$ is alkyl or phenyl, preferably 1 to 4 carbon alkyl or phenalkyl; Z, taken with N, represents the carbon atoms necessary to make up benzthiazole radical; X is an acid anion; and n is 1 when $R^5$ carries a negative charge and 2 when $R^5$ is electrically neutral.

The anion designated X represents those anionic radicals customary in the art, for example, chloride, bromide, iodide, p-toluene sulfonate, acetate, propionate, nitrate, sulfate, etc. Preferably, the anion is the fluorosulfonate radical $·FSO_3^-$.

As stated above, the compounds of the present invention are normally inert with respect to silver halide and substantially colorless. Upon contact with an alkaline processing composition the chromophoric group is generated. The following equation illustrates the reaction which the compounds of the present invention undergo.

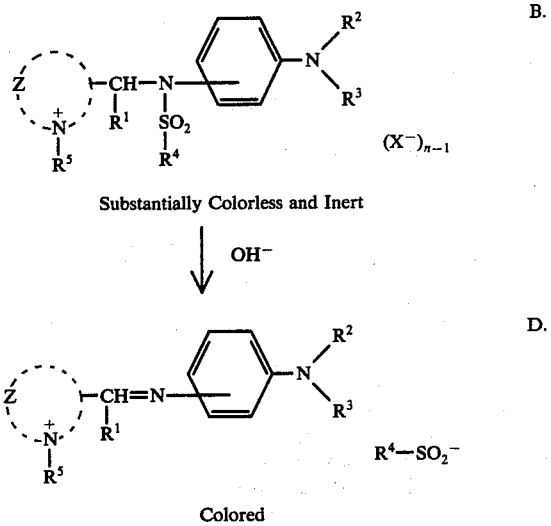

From the foregoing equation it will be seen that the base of alkaline processing composition serves to release the alkyl or aryl sulfonic acid to generate the chromophoric group C=N forming a colored compound known to the art to be a strong desensitizer for silver halide.

As examples of specific compounds within the scope of the present invention mention may be made of the following:

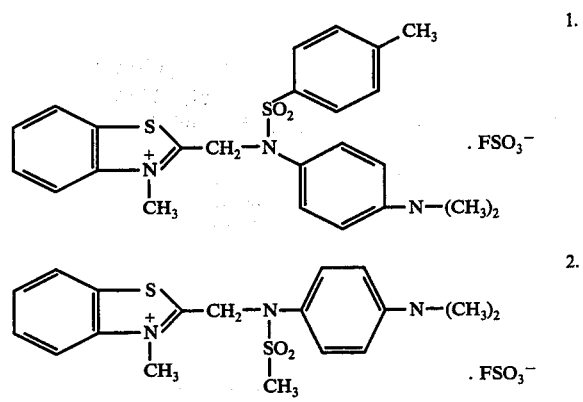

The following non-limiting examples illustrate the preparation of the desensitizing agent precursors of the present invention.

EXAMPLE I

Compound No. 1 was prepared by dissolving

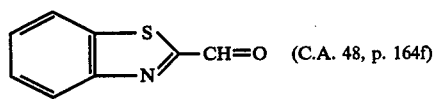

(2.7 g.) and N,N-dimethyl-p-phenylenediamine (5.0 g.) in 25 ml. of toluene and refluxing the mixture for 2 hours. The mixture was filtered and cooled and the solid was washed with cold water giving 2.6 g. of

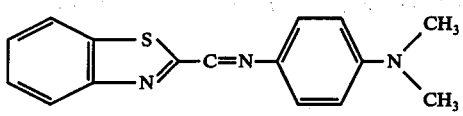

m. p. 173°–175° C.

Analysis: Calculated C, 68.38 H, 5.38 N, 4.96 S, 11.41; Found C, 68.06 H, 5.30 N, 4.79 S, 11.36.
which was reduced using Raney nickel in ethyl acetate to provide

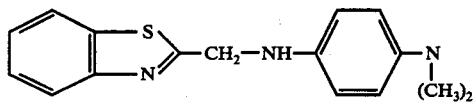

m. p. 93.5°–95° C.

Analysis: Calculated C, 67.90 H, 6.06 N, 14.85 S, 11.33; Found C, 67.91 H, 5.95 N, 14.78 S, 11.07.

The last-mentioned compound (1.0 g.) was dissolved in 10 ml. of pyridine and 1.5 g. p-toluene sulfonyl chloride was added. The mixture was stirred for 15 minutes. Water was added to precipitate

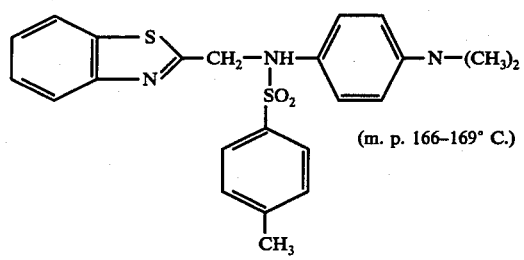

(m. p. 166–169° C.)

The last-named compound was quaternized in ethyl acetate using 2.36 g. of the compound in 100 ml. of ethyl acetate and 500 mg. of methylfluorosulfonate. The mixture was allowed to stand for 15 minutes. The supernatant liquid was decanted, an equal volume of ether added and the mixture allowed to stand overnight. Compound No. 1 was filtered off and found to melt at 104°–107° C.

EXAMPLE II

The procedure and materials of Example I were repeated except that methane sulfonyl chloride was employed instead of p-toluenesulfonyl chloride to produce a microcrystalline solid, Compound No. 2.

Since certain changes may be made in the above compositions without departing from the scope of the invention herein involved, it is intended that all matter contained in the above description should be interpreted as illustrative and not in a limiting sense.

What is claimed is:

1. A compound represented by the formula:

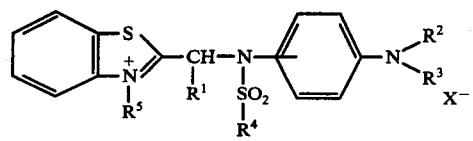

wherein $R^1$ is hydrogen or 1 to 4 carbon alkyl; $R^2$, $R^3$ and $R^5$ is 1 to 4 carbon alkyl; $R^4$ is 1 to 4 carbon alkyl, phenyl or ($C_1$-$C_{12}$ alkyl) phenyl; and X is an acid anion.

2. The compound as defined in claim 1 wherein $R^2$ and $R^3$ are methyl groups.

3. The compound as defined in claim 1 wherein $R^2$ and $R^3$ are ethyl groups.

4. The compound as defined in claim 1 wherein $R^4$ is

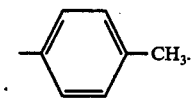

5. The compound as defined in claim 1 wherein $R^4$ is

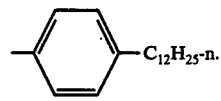

6. The compound as defined in claim 1 wherein $R^5$ is methyl.

7. The compound as defined in claim 1 wherein $R^5$ is ethyl.

8. The compound as defined in claim 1 wherein said compound is:

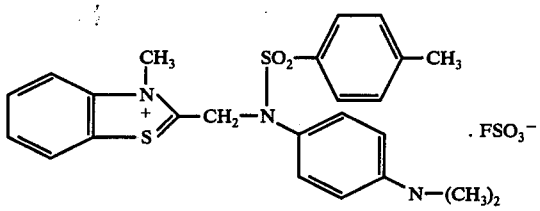

* * * * *